(12) United States Patent
Strong et al.

(10) Patent No.: US 8,034,803 B2
(45) Date of Patent: Oct. 11, 2011

(54) PHOTODYNAMIC THERAPY OF OCCULT AGE-RELATED MACULAR DEGENERATION

(75) Inventors: H. Andrew Strong, North Vancouver (CA); Mohammad Azab, West Vancouver (CA); Yong Hao, Vancouver (CA); John Miller Koester, Duluth, GA (US); Troy Albert Reaves, Jr., Alpharetta, GA (US)

(73) Assignees: QLT Inc., Vancouver, BC (CA); Novartis, A.G., Basel (CH)

( * ) Notice: Subject to any disclaimer, the term of this patent is extended or adjusted under 35 U.S.C. 154(b) by 649 days.

(21) Appl. No.: 10/072,272

(22) Filed: Feb. 6, 2002

(65) Prior Publication Data

US 2003/0087889 A1    May 8, 2003

Related U.S. Application Data

(60) Provisional application No. 60/266,940, filed on Feb. 6, 2001.

(51) Int. Cl.
  *A01N 55/02*   (2006.01)
  *A01N 43/38*   (2006.01)
  *A61K 31/555*  (2006.01)
  *A61K 31/40*   (2006.01)

(52) U.S. Cl. ........................................ 514/185; 514/410

(58) Field of Classification Search .................... 424/9.6, 424/9.61; 514/185, 410
  See application file for complete search history.

(56) References Cited

U.S. PATENT DOCUMENTS 5,798,349 A * 8/1998 Levy et al. .................... 514/185
5,935,942 A   8/1999 Zeimer .......................... 514/63

OTHER PUBLICATIONS

Drug Facts and Comparison 1999, p. 3987.*
TAP Report 1, ("Photodynamic Therapy of Subfoveal Choroidal Neovascularization in Age-related Macular Degeneration with Verteporfin." Arch Ophtalmol.1999; 117:1329-1345) (the TAP Report).*
Reg # 129497-78-5, ACS copyright 2005.*
Costa, R. et al. "Photodynamic Therapy with Indocyanine Green for Occult Subfoveal Choroidal Neovascularization Caused by Age-Related Macular Degeneration" [Abstract] Current Eye Research 23(4):271-275 (2001).
Husain, D. et al "Photodynamic Therapy of Exudative Age-Related Macular Degeneration" Seminars in Opthalmology 12(1):14-25 (1997).
Macular Photocoagulation Study Group. "Subfoveal Neovascular Lesions in Age-Related Macular Degeneration" Arch. Opthalmol 109:1242-1257 (1991).
Treatment of Age-Related Macular Degeneration with Photodynamic Therapy (TAP) Study Group. "Photodynamic Therapy of Subfoveal Choroidal Neovascularization" Arch. Opthalmol. 117(10):1329-1345 (1999).
Verteporfin in Photodynamic Therapy Study Group: "Verteporfin Therapy of Subfoveal Choroidal Neovascularization in Age-Related Macular Degeneration: Two-Year Results of a Randomized Clinical Trial Including Lesions with Occult with No Classic Choroidal Neovascularization: Verteporfin in Photodynamic Therapy Report 2" American Journal of Opthalmology 131(5):541-560 (2001).
Wormald, R. et al. "Photodynamic Therapy for Neovascular Age-Related Macular Degeneration" [Abstract] Cochrane Database of Systematic Reviews (Online: Update Software) England 2000 2:CD002030 (2000).

* cited by examiner

*Primary Examiner* — Yong Chong
(74) *Attorney, Agent, or Firm* — Morrison & Foerster LLP (57) ABSTRACT

The invention relates to the selection and treatment of subjects afflicted with occult choroidal neovascular lesions, including subjects with age-related macular degeneration, by use of photo dynamic therapy (PDT).

17 Claims, 2 Drawing Sheets

PHOTODYNAMIC THERAPY OF OCCULT AGE-RELATED MACULAR DEGENERATION

This application claims benefit of priority from U.S. Provisional Patent Application No. 60/266,940 filed Feb. 6, 2001, which is hereby incorporated by reference as if fully set forth.

TECHNICAL FIELD

The invention relates to a method to treat occult age-related macular degeneration by administering photodynamic therapy (PDT) to the eye.

BACKGROUND OF THE INVENTION

Age-related macular degeneration (AMD) causes severe, irreversible vision loss and is the leading cause of blindness in individuals older than 50 years in the Western World. The Framingham study reported the prevalence of AMD in the United States as 1.2% of the population between 52 and 64 years of age, with an increase to 20% in patients over the age of 75. The Beaver Dam Eye Study reported an incidence of 37% in patients 75 years and older. Most patients have the non-neovascular ("dry") form, characterized by drusen and atrophic changes in the retinal pigment epithelium (RPE). Eighty to ninety percent of the severe vision loss due to AMD, however, is attributable to the form characterized by choroidal neovascularization (CNV), also called "wet" AMD. CNV is an ingrowth of choroidal capillaries through a break in the outer aspects of Bruch's membrane. In the United States, between 70,000-200,000 individuals over the age of 65 develop the wet form of AMD every year. Slightly lower estimates of prevalence and incidence of CNV secondary to AMD have been reported in the Netherlands but higher estimates have been found in England. The great majority of wet AMD occurs subfoveally.

CNV in wet AMD can be generally divided into two classes, "classic" CNV and "occult" CNV. The two forms are distinguishable by angiography conducted with fluorescein dye. Classic CNV is generally defined by a well-demarcated area of bright hyperfluorescence throughout the transit phase of the angiogram with leakage in the mid and late phase frames. Vessels of the neovascular lesion often will be visualized in the early phase of the angiogram, but are not required to be identified. Occult CNV includes fibrovascular pigment epithelial detachment (a type of occult choroidal neovascularization in which areas of irregular elevation of the retinal pigment epithelium are detectable on stereoscopic angiography and consists of an area of stippled hyperfluorescence noted within 1 to 2 minutes after fluorescein injection). Persistence of fluorescein staining or leakage within this area occurs within 10 minutes after fluorescein injection. These areas are not as discrete or bright as areas of classic choroidal neovascularization or serious detachment of the retinal pigment epithelium in the early phase of the angiogram. In addition, occult CNV may show late leakage of an undetermined source (a type of occult choroidal neovascularization in which areas of leakage at the level of the retinal pigment epitherim in the late phase of the angiogram are without well-demarcated areas of hyperfluorescence from classic CNV or a fibrovascular pigment epithelial detachment discernible in the early phase of the angiogram that account for the leakage.) A detailed description of classic and occult CNV lesions appears in Arch. Ophthalmol. 1991; 109: 1242-1257. Although no formal studies are available on the prevalence of lesion subtypes, it is estimated that patients with occult lesions represent 60-80% of all patients who present with subfoveal neovascular AMD.

A CNV lesion can be comprised only of occult CNV, which is termed occult CNV with no classic CNV. Some lesions comprise both classic and occult CNV. A lesion in which the area of classic CNV occupies more than 0%, but less than 50% is termed "minimally classic". A lesion in which the area of classic CNV occupies at least 50% of the area of the entire lesion is termed "predominantly classic."

In CNV, the newly formed vessels have a tendency to leak blood and fluid, causing symptoms of scotoma and metamorphopsia. The new vessels are accompanied by proliferation of fibrous tissue. This complex of new vessels and fibrous tissue can destroy photoreceptors within 3 to 24 months. At the same time that existing CNV is destroying retinal tissue where it has formed, the lesion can continue to grow throughout the macula, resulting in progressive, severe and irreversible vision loss. Without treatment, most affected eyes will have poor central vision (<20/200) within 2 years. In addition, when one eye of an individual develops CNV, the fellow eye has about a 50% chance of developing a similar CNV lesion within 5 years.

At present, there are no proven treatment options for CNV characterized by occult with no classic lesions, or minimally classic lesions. Laser photocoagulation is limited to selected cases because the treatment destroys any viable photoreceptors overlying the area affected by CNV, often resulting in immediate visual acuity loss, especially when the lesion is subfoveal and the visual acuity is 20/200 or better. For this reason, laser photocoagulation is only indicated for well-demarcated extrafoveal and juxtafoveal CNV lesions as well as small, well-demarcated subfoveal lesions that have a pattern of classic CNV on fluorescein angiography. Recurrences following standard laser treatment of AMD cases occur in approximately 50% of cases. The recurrent CNV can lead to further vision loss, especially when the originally treated lesion was extrafoveal or juxtafoveal.

Photodynamic therapy (PDT) with verteporfin (VISUDYNE™, Novartis Ophthalmics) offers an approach to selectively destroy CNV without significant destruction of overlying retina tissue, possibly by occluding the new vessels within the CNV lesion. Photodynamic therapy is a two-step process consisting of an intravenous injection of a photosensitizer (light-activated drug) followed by light application. The light sources most commonly used are non-thermal lasers or light emitting diodes (LEDs). Verteporfin preferentially accumulates in neovascular tissues, including the endothelial cells of choroidal neovascularization. In combination with localized light administration, this allows for selective treatment of the pathologic tissue. After exposure to light at a wavelength of 689 nm, an energy transfer cascade is initiated, culminating in the formation of singlet oxygen which generates intracellular free radicals. These free radicals can disrupt cellular structures such as the cell membrane, mitochondria, and lysosomal membranes.

Occlusion of the neovasculature is presumed to be the major mechanism of PDT with verteporfin. Occlusion can occur through free radical damage to the endothelial cells, causing subsequent platelet adhesion and degranulation, and thrombus formation. A reduction in blood flow from the new vessels may lead to a confinement in the growth of the fibrovascular CNV lesion with subsequent reduced risk of further vision loss compared with no treatment. Thus, verteporfin PDT reduces the area of the macula affected by CNV and spares viable photoreceptors from destruction caused by fibrovascular disorganization of the outer retina.

Photodynamic therapy of neovascular conditions in the eye has been attempted over the past several years using a variety of photosensitive compounds, e.g. porphyrin derivatives, such as hematoporphyrin derivative and porfimer sodium (PHOTOFRIN® Axcan Pharmaceuticals), phthalocyanines, green porphyrins (such as verteporfin, also known as BPD-MA), purpurins, such as tin ethyl etiopurpurin and texaphyrins, such as motexafin lutetium. The photosensitive compound verteporfin (Visudyne™, Novartis Ophthalmics) is the only photosensitive compound to have received regulatory approval (from the U.S. Food and Drug Administration (FDA) and corresponding agencies approximately 30 other countries) for the treatment of CNV, but has only proven its efficacy in clinical trials in the predominantly classic form of the disease (see Arch. Ophthalmol. 1999; 117: 1329-1345) Hence, there is still no approved PDT treatment for AMD patients having predominantly occult, rather than classic, lesions.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

DISCLOSURE OF THE INVENTION

The invention is directed to a method to treat occult CNV lesions using photodynamic therapy. "Occult lesions" as used herein refer to CNV lesions which have an occult CNV component, preferably comprising 50% to 100% of the lesion, and lesions that are defined as minimally classic that have an occult component. CNV characterized by lesions having an occult component comprising at least about (and including) 50% to about (and including) 100% of the lesion may be herein referred to as "occult CNV." Results of a study outlined in Example 3 below show that subjects having occult lesions respond to PDT carried out using the photoactive compound verteporfin. This was surprising, in view of a study (Arch Ophthalmol. 117: 1329-1345 by the TAP Study Group), which showed that lesions classified as predominantly classic had a large treatment benefit with verteporfin PDT, whereas lesions classified as minimally classic did not. Furthermore, lesions which had evidence of occult CNV did not appear to benefit (see Table 5 of the TAP Study Group Report, cited above). Subgroup analysis of a group having "no classic" CNV did benefit, but the numbers of subjects were small, and the interpretation of this result was somewhat confusing in light of the lack of apparent benefit in minimally classic subjects. Subgroup analysis of the occult subject population in Example 3 below has unexpectedly revealed the criteria for determining which subjects having occult CNV will benefit most from Visudyne therapy, at least under certain conditions, as follows.

Subjects can be divided on the basis of best corrected visual acuity prior to treatment (baseline visual acuity) into those having poor visual acuity prior to treatment and those having relatively good visual acuity. Poor visual acuity means generally a best corrected vision of less than 65 letters on an ETDRS chart (see Example 1 below), corresponding to a visual acuity of less than about 20/50 or worse. Good visual acuity generally means a best corrected vision of at least 65 letters, corresponding to a visual acuity of about 20/50 or better. All subjects having poor visual acuity at baseline had a great benefit from PDT treatment of their CNV lesion. However, subjects having good visual acuity prior to treatment, benefit from PDT treatment if the size of their lesion is small, generally less than about 4-5 Disc Areas (see Example 2 below), which corresponds to a lesion size of less than about 10 to 13 mm$^2$. Subjects having good visual acuity and large lesion size larger lesion size do not appear to benefit from treatment with PDT compared to placebo controls. All subjects having a small lesion size benefited from treatment. This was a very surprising result, because there was no reason to anticipate this differential pattern of response to PDT. Without being bound by theory, the expectation might have been that subjects having larger lesions generally would experience a greater benefit of PDT than those having smaller lesions. Having discovered the sub-populations of occult subjects that benefit from PDT, it has been possible to design a method to treat occult CNV so that the chances of preserving visual acuity in treated subjects is substantial.

In one aspect, the invention is directed to a method of treating a subject having an occult choroidal neovascular lesion, comprising the steps of:
  assessing the size of the lesion,
  determining the best corrected visual acuity of the subject,
  selecting for treatment of a subject having either or both of
    (a) a small lesion or (b) poor visual acuity, and
  providing photodynamic therapy (PDT) to the lesion.

Stated differently, the invention provides methods for treating an occult choroidal neovascular lesion in a subject comprising providing photodynamic therapy to a subject assessed as having either or both of (a) a small lesion or (b) poor visual acuity. The assessment of the subject may be by determining the size of said lesion and/or determining the best corrected visual acuity of the subject.

As recognized in the art, PDT comprises the steps of
  administering to the subject an amount of a formulation of a photoactive compound sufficient to permit an effective amount to accumulate in the lesion of the subject,
  permitting sufficient time to elapse to allow an effective amount of the photoactive compound to localize in the lesion; and
  irradiating the lesion with light absorbed by the photoactive compound.

Preferably, the subject is evaluated angiographically for evidence of new neovascular leakage at least every three months, and if new leakage has occurred, the PDT treatment is repeated.

Preferably, the visual acuity of the subject at baseline is less than about (and including) 65 letters in the practice of the invention.

Also preferred in the practice of the invention are conditions wherein the small lesion size is less than about 4-5 disc areas, most preferably less than about 4 Disc Areas.

A particular embodiment useful for PDT treatment of predominantly classic CNV with verteporfin includes the administration by infusion of verteporfin in a liposomal formulation know as Verteporfin for Injection (VFI) over a period of 10 minutes, and subsequent irradiation with light at a wavelength of (689+/−3 nm) that activates the verteporfin at approximately 15 minutes after the start of the infusion. Animal studies have demonstrated that the elapsed time between drug administration and light is a very important variable in the treatment of neovascular conditions with PDT (see U.S. Pat. No. 5,770,619). Pharmacokinetic studies have shown that photosensitive compound accumulates preferentially in neovasculature, but eventually permeates other tissue as well. To achieve maximal selectivity between normal tissue and neovasculature, it is important to apply light to a CNV lesion when sufficient a amount of photosensitive has reached the lesion. Without being bound by theory, the present invention is based in part upon the recognition that with occult lesions, which are more fibrous, delaying light application slightly improves the outcome of treatment. Thus in another aspect, the invention is directed to the above method wherein the administration of light is delayed until about 30 minutes after the start of administration of the photoactive compound.

In another aspect, the invention is directed to a method of selecting subjects having an occult choroidal neovascular lesion who will benefit from photodynamic therapy, comprising:
(a) assessing size of the lesion
(b) obtaining a best corrected visual acuity measurement for the subject, and
(c) selecting subjects for treatment having either or both of (i) small or (ii) poor visual acuity

MODES OF CARRYING OUT THE INVENTION

The present invention is generally directed to treating occult choroidal neovascularization (CNV) lesions with photodynamic therapy (PDT). In the general approach that forms the subject matter of the invention, a human patient who has been diagnosed with occult CNV, is suspected of having, or is otherwise afflicted with occult CNV is assessed angiographically to determine the size of the CNV lesion. The patient is also assessed for best corrected visual acuity. If the subject has either or both of (a) a lesion size of less than about 4-5 Disc Areas, or (b) a best corrected visual acuity of less than about 65 letters, then the subject is identified as being a candidate for treatment with photodynamic therapy. The patient is then administered a suitable photoactive compound in amount sufficient to provide an effective concentration of the photoactive compound to localize in the target neovasculature. After a suitable time period to permit an effective concentration of the compound to accumulate in the ocular neovasculature, this region is irradiated with light absorbed by the photoactive compound. The irradiation results in excitation of the compound which, in turn, causes damage to the immediately surrounding tissue, which results in closure of neovasculature, and cessation of leakage. This procedure is repeated as required based upon periodic angiographic evaluations.

The invention utilizes PDT methods which generally include the administration of a photosensitizer (PS) and irradiation with a wavelength of electromagnetic radiation capable of activating the PS. The invention also includes use of a PS in the preparation of a medicament for use in any of the methods described herein.

Assessment of Visual Acuity

"Visual acuity" as used herein means best corrected visual acuity. At a baseline examination, conducted prior to any treatment, visual acuity is assessed. Preferably the assessment is done using a retroilluminated Lighthouse for the Blind (New York, N.Y.) distance visual acuity test chart, using modified Early Treatment Diabetic Retinopathy Study (ETDRS) charts 1, 2, and R), the methodology for which is outlined in detail in Example 1 below. Another chart, such as a typical Snellen eye chart can also be used if an ETDRS chart is not available. However, an ETDRS chart is preferred, as it gives a more precise measurement of visual acuity. The use of ETDRS eye charts in determining visual acuity is explained in Arch. Ophthalmol. 1991 109: 1242-1257, which is incorporated herein in its entirety.

The ETDRS charts have 5 letters per line and a doubling of the minimum angle of resolution every 3 lines. Best corrected visual acuity is scored based on the total number of correct letters identified at a distance of 2 meters, plus 15. If a subject reads fewer than 20 letters at 2 meters, the subject is tested on the top 3 lines at 1 meter, and the score is the total number of letters read at 2 meters plus the total number of letters read a 1 meter. A visual acuity score of 65 and 73 letters corresponds to about 20/50 and 20/40, respectively, on a Snellen eye chart. A visual acuity of 34 letters corresponds to 20/200.

Potential candidates for photodynamic therapy, as described herein, may have a best corrected visual acuity score of about 65 letters or less (unless the size of their lesion is small, as described below). As will be evident from Example 1 below, determining the visual acuity of a subject is not a precise measurement, and can vary from day to day for reasons having to do with the subject's general health or mood. Therefore, it is likely that such measurements will vary by approximately + or −10% or so, and the figure of 65 letters or less is meant to encompass such deviations.

Assessment of Lesion Size

Lesion size may be determined by reference to angiographic photographs taken in rapid succession after the injection of fluorescein dye, as is commonly known in the art. A drawing of the lesion, including all of its components can be made by projecting the film on a microfilm reader using techniques described in Arch. Ophthahnol. 1991 109: 1242-1257. Such a drawing can be used for estimating the size of a lesion. Generally, lesion size is calculated in terms of "Disc Areas" (DA) which is a number corresponding to the entire area of a lesion, rather than to the diameter of the lesion, because a lesion is usually not perfectly round. The size of a lesion for the purposes of this invention refers to the entire neovascular lesion, which may be considered to be constituted by the entire complex of lesion components, including a choroidal neovascularization (classic or occult), thick blood, elevated blocked fluorescence (due to a pigment or scar that obscures the neovascular borders), and serous detachments of the retinal pigment epithelium. The number of disc areas covered by a lesion can be determined by reference to a graded series of "circles" of a defined diameter provided on a transparent overlay, which can be superimposed on the angiograph, as described in. in Arch. Ophthalmol. 1991 109: 1242-1257. The transparency is placed on the 35 mm frame of the angiogram (made using a 30 fundus camera). A lesion size of 1 DA corresponds to an area of 2.5 square millimeters, assuming a disc diameter of 1.6 millimeters. A lesion size of 9 DA corresponds to an area of 5.4 square millimeters. Other methods of comparatively grading lesion sizes can be devised by those skilled in the art. A detail example of how to assess lesion size appears in Example 2 below.

For the purposes of the invention, it is possible but not necessary to draw a distinction between small lesions and larger lesions. A small lesion is generally smaller than about 5 Disc areas (corresponding to an lesion having an area in the eye of about 13 $mm^2$), and preferably no larger than about 4 DA areas (corresponding to an lesion having an area in the eye of about 10 $mm^2$). However, it is understood, by reference to Example 2 below that determining the lesion size is not a precise art, especially when the lesion has an irregular shape, and that for example, a lesion measured as 5.5 DA might be considered a small lesion under some circumstances. A table showing the conversion of DA to area of lesion is found in Table 1 below.

Photoactive Compounds

The photodynamic therapy according to the invention can be performed using any of a number of photoactive compounds. For example, various derivatives of hematoporphyrin have been described, including improvements on hematoporphyrin derivative per se such as those described in U.S. Pat. Nos. 5,028,621; 4,866,168; 4,649,151; and 5,438,071, the entire contents of which are incorporated herein by reference. In addition, pheophorbides are described in U.S. Pat. Nos. 5,198,460; 5,002,962; and 5,093,349; bacteriochlorins in U.S. Pat. Nos. 5,171,741 and 5,173,504. The contents of these patents are also incorporated herein by reference. In addition, U.S. Pat. No. 5,079,262 describes the use of a precursor to hematoporphyrin, aminolevulinic acid (ALA), as the source of a photoactive compound. The use of phthalocyanine photosensitive compounds in photodynamic therapy is described in U.S. Pat. No. 5,166,197. The contents of all of the foregoing patents are incorporated herein by reference. Other possible photoactive compounds include purpurins (such as tinethyl etiopurpurin), merocyanines, iminochlorinaspartic acid derivative (U.S. Pat. No. 6,063,777), texaphyrins (such as motexafin lutetium) and porphycenes. Particular preferred photoactive compounds for use in the invention method are the green porphyrins. These porphyrins are described in U.S. Pat. Nos. 4,883,790; 4,920,143; 5,095,030; and 5,171,749, the entire contents of which are incorporated herein by reference. As these photoactive agents represent a particularly preferred embodiment, typical formulas for these compounds are represented herein in FIG. 1.

Referring to FIG. 1, and in preferred embodiments, each of $R^1$ and $R^2$ is independently selected from the group consisting of carbalkoxyl (2-6C), alkyl (1-6C), arylsulfonyl (6-10C), cyano and —$CONR^5CO$ wherein $R^5$ is aryl (6-10C) or alkyl (1-6C); each $R^3$ is independently carboxyl, carboxyalkyl (2-6C) or a salt, amide, ester or acylhydrazone thereof or is alkyl (1-6C); $R^4$ is CH=$CH_2$ or —CH($OR^{4'}$)$CH_3$ wherein $R^{4'}$ is H, or alkyl (1-6C) optionally substituted with a hydrophilic substituent. Especially preferred also are green porphyrins of the formula shown in FIG. 1C or 1D or mixtures thereof.

Figure 1A:
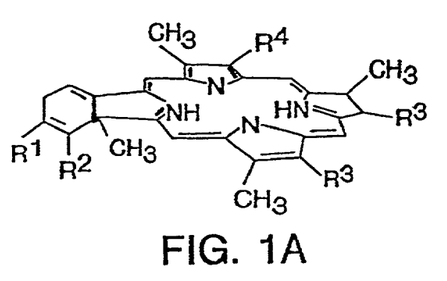
FIG. 1 is a drawing of preferred forms of the green porphyrins useful in the methods of the invention.
Figure 1B:
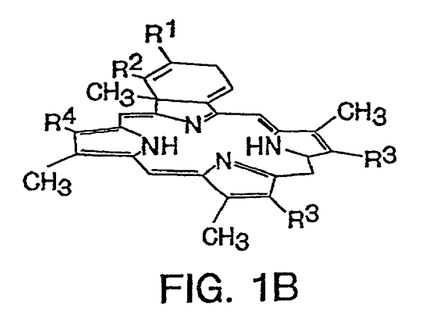
Figure 1C:
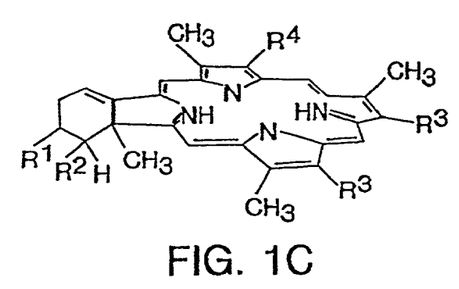
Figure 1D:
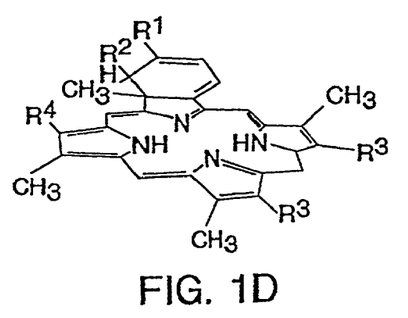
Figure 1E:
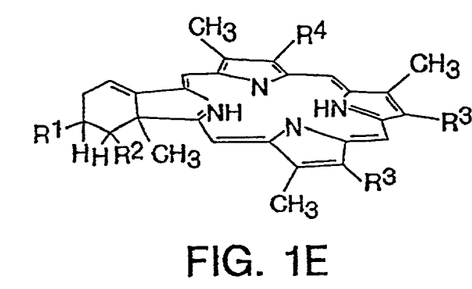
Figure 1F:
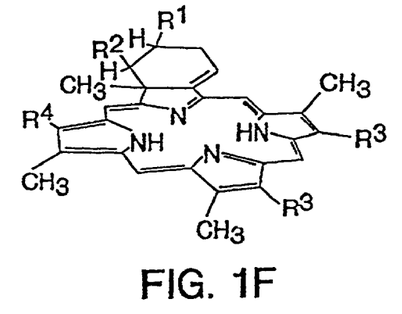

More preferred are embodiments are those wherein the green porphyrin is of the formula shown in FIG. 1C or 1D or a mixture thereof and wherein each of $R^1$ and $R^2$ is independently carbalkoxyl (2-6C); one $R^3$ is carboxyalkyl (2-6C) and the other $R^3$ is an ester of a carboxyalkyl (2-6C) substituent; and $R^4$ is CH=$CH_2$ or —CH(OH)$CH_3$.

Still more preferred are embodiments wherein green porphyrin is of the formula shown in FIG. 1C and wherein $R^1$ and $R^2$ are methoxycarbonyl; one $R^3$ is —$CH_2CH_2COOCH_3$ and the other $R^3$ is $CH_2CH_2COOH$; and $R^44$ is CH=$CH_2$; i.e., BPD-MA.

Particularly preferred green porphyrins for the practice of the invention are compounds such as BPD-DA, -DB, -MA, and -MB, and in particular BPD-MA, EA6, and B3. These compounds are porphyrin derivatives obtained by reacting a porphyrin nucleus with an alkyne in a Diels-Alder type reaction to obtain a monohydrobenzoporphyrin as described in U.S. Pat. No. 5,171,749, which is hereby incorporated in its entirety by reference. Other photosensitizers that may be used in the present invention include those described in U.S. Pat. Nos. 5,308,608, 6,093,739, 5,703,230, 5,831,088, 5,726,304, and 5,405,957.

It is preferred that the absorption spectrum of the photoactive compound be in the visible range, typically between 350 nm and 1200 nm, more preferably between 400-900 nm, and even more preferably between 600-900 nm. Generally, any polypyrrolic macrocyclic photoactive compound may be used in the practice of the invention.

As used herein, the terms "photosensitizer," "photosensitive compound," "PS," and "photoactive compound(s)" are used interchangeably. Any variation in meaning between these terms is not meant to depart form the gist and scope of the claimed invention.

Particularly preferred PSs are the green porphyrins, such as BPD-DA, -DB, -MA, and -MB, and in particular BPD-MA, EA6, and B3. These compounds are porphyrin derivatives obtained by reacting a porphyrin nucleus with an alkyne in a Diels-Alder type reaction to obtain a monohydrobenzoporphyrin, and they are described in detail in the issued U.S. Pat. No. 5,171,749, which is hereby incorporated in its entirety by reference. Of course, combinations of photosensitizers may also be used.

Figure 2:
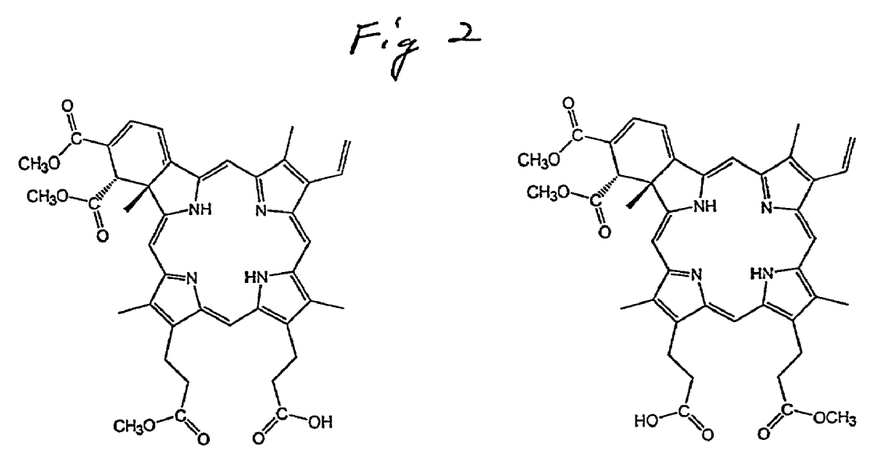
FIG. 2 is a drawing of the chemical structure of verteporfin, which has two regioisomers.

Representations of BPD-MA$_C$ and BPD-MA$_D$, which are the components of Verteporfin, as well as illustrations of A and B ring forms of EA6 and B3, are as follows:

-continued

B-EA6

A-B3

B-B3

Further examples of other photosensitizers for use in the present invention include, but are not limited to, angelicins, some biological macromolecules such as lipofuscin; photosystem II reaction centers; and D1-D2-cyt b-559 photosystem II reaction centers, chalcogenapyrillium dyes, chlorins, chlorophylls, coumarins, cyanines, ceratin DNA and related compounds such as adenosine; cytosine; 2'-deoxyguanosine-5'-monophosphate; deoxyribonucleic acid; guanine; 4-thiouridine; 2'-thymidine 5'-monophosphate; thymidylyl (3'-5')-2'-deoxyadenosine; thymidylyl(3'-5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, fullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one; N-formylkynurenine; kynurenic acid; kynurenine; 3-hydroxykynurenine; DL-3-hydroxykynurenine; sanguinarine; berberine; carmane; and 5,7,9(11),22-ergostatetraene-3 β-ol, nile blue derivatives, NSAIDs (non-steroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol,* 70(4):391-475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin; 6,4,4'-trimethyl angelicin; 6,4',5'-trimethyl angelicin; 4,6,4',5'-tetramethyl-1'-thioangelicin; and 4,6,4',5'-tetramethyl angelicin.

Exemplary chalcogenapyrillium dyes include pyrilium perchlorate, 4,4'-(1,3-propenyl)-bis[2,6-di(1,1-dimethyl-ethyl)]-; pyrilium perchlorate, 2,6-bis(1,1-dimethyl-ethyl)-4-[1-[2,6-bis(1,1-dimethyl-ethyl)selenopyran-4-ylidene]-3-propenyl-; pyrilium hexofluoro phosphate, 2,6-bis-(1,1-dimethyl-ethyl)-selenopyran-4-ylidene]-3-propenyl-; pyrilium hexofluoro phosphate, 2,6-bis(1,1-dimethyl-ethyl)-selenopyran-4-ylidene]-3-propenyl-; pyrilium perchlorate, 2,6-bis(1,1-dimethyl-ethyl)-4-[1-[2,6-bis(1,1-dimethyl-ethyl)telluropyran-4-ylidene]-3-propenyl-; pyrilium hexofluoro phosphate, 2,6-bis(1,1-dimethyl-ethyl)-4-[1-[2,6-bis(1,1-dimethyl-ethyl)telluropyran-4-ylidene]-3-propenyl-; pyrilium perchlorate, 2,6-bis(1,1-dimethyl-ethyl)-4-[1-[2,6-bis(1,1-dimethyl-ethyl)thiapyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; selenopyrilium, 2,6-bis(1,1-dimethylethyl)-4-[1-[2,6-bis(1,1-dimethylethyl)selenopyran-4-ylidene]-3-propenyl]-; selenopyrilium percheorate, 2,6-bis(1,1-dimethyl-ethyl)-4-[1-[2,6-bis(1,1-dimethyl-ethyl)-4-[1-[2,6-bis(1,1-dimethyl-ethyl)telluropyran -4-ylidene]-3-propenyl]-; selenopyrilium hexofluoro phosphate, 2,6-bis(1,1-dimethyl-ethyl)-4-[1-[2,6-bis(1,1-dimethyl-ethyl) telluropyran-4-ylidene]-3-propenyl]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-butenyl)]-; selenopyrilium hexofluoro phosphate, 2,6-bis(1,1-dimethyl-ethyl)-4-[2-[2,6-bis(1,1-dimethyl-ethyl) selenopyran-4-ylidene]-4-(2-pentenyl)]-; telluropyrilium tetrafluoroborate, 2,6-bis(1,1-dimethylethyl)-4-[1-[2,6-bis(1,1-dimethyl-ethyl)-telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]ethyl-; telluropyrilium hexofluoro phosphate, 2,6-bis(1,1-dimethyl-ethyl)-4-[1-[2,6-bis(1,1-dimethyl-ethyl)-telluropyran-4-ylidene]methyl-; thiopyrilium hexofluoro phosphate, 2,6-bis(1,1-dimethyl-ethyl)-4-[1-[2,6-bis(1,1-dimethyl-ethyl)

thiopyran-4-ylidene]-3-propenyl]-; thiopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; and thiopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-.

Exemplary chlorins dyes include 5-azachlorin dimethyl ester derivative; 5,10,15,20-tetrakis-(m-hydroxyphenyl) bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethylester; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin e6 dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethylamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl) chlorin; meta-(tetrahydroxyphenyl)chlorin; methyl-$13^1$-deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlorin; tin (IV) chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcoumarin; 5,7-dimethoxy-3-(1-naphthoyl) coumarin; 6-methylcoumarin; 2H-selenolo[3,2-g] [1] benzopyran-2-one; 2H-selenolo[3,2-g] [1] benzothiopyran-2-one; 7H-selenolo[3,2-g] [1] benzoselenopyran-7-one; 7H-selenopyrano[3,2-f] [1] benzofuran-7-one; 7H-selenopyrano[3,2-f] [1] benzo-thiophene-7-one; 2H-thienol[3,2-g] [1] benzopyran-2-one; 7H-thienol[3,2-g] [1] benzothiopyran-7-one; 7H-thiopyrano[3,2-f] [1] benzofuran-7-one; coal tar mixture; khellin; RG 708; RG277; and visnagin.

Exemplary cyanines include benzoselenazole dye; benzoxazole dye; 1,1'-diethyloxacarbocyanine; 1,1'-diethyloxadicarbocyanine; 1,1'-diethylthiacarbocyanine; 3,3'-dialkylthiacarbocyanines (n=2–18); 3,3'-diethylthiacarbocyanine iodide; 3,3'-dihexylselenacarbocyanine; kryptocyanine; MC540 benzoxazole derivative; MC540 quinoline derivative; merocyanine 540; and meso-ethyl, 3,3'-dihexylselenacarbocyanine.

Exemplary fullerenes include $C_{60}$; $C_{70}$; $C_{76}$; dihydro-fullerene; 1,9-(4-hydroxy-cyclohexano)-buckminster-fullerene; [1-methyl-succinate-4-methyl-cyclohexadiene-2,3]-buckminster-fullerene; and tetrahydro fullerene.

Exemplary metalloporphyrins include cadmium (11) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso(4-sulfonatophenyl)-porphine; Europium (III) dimethyltexaphyrin dihydroxide; gallium tetraphenylporphyrin; iron meso-tetra(4-N-methylpyridyl)-porphine; lutetium (III) tetra(N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methylpyridyl)-porphine; nickel meso-tetra(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin meso-tetra-(4-N-methylpyridyl)-porphine; tin meso-tetra(4-sulfonatophenyl)-porphine; tin (IV) tetrakis(4-sulfonatophenyl) porphyrin dichloride; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-(1,1-dimethyl-ethyl)tetranaphtho(2,3-b:2',3'-g:2"3"-1:2'"3"'-q)porphyrazine; zinc (II) 2-(3-pyridyloxy)benzo[b]-10,19,28-tri(1,1-dimethylethyl)trinaphtho[2',3'-g:2"3"1::2'",3'"-q] porphyrazine; zinc (II) 2,18-bis-(3-pyridyloxy)dibenzo[b,1]-10,26-di(1,1-dimethyl-ethyl)dinaphtho[2',3'-g:2'",3'"-q]porphyrazine; zinc (II) 2,9-bis-(3-pyridyloxy)dibenzo[b,g]-17,26-di(1,1-dimethyl-ethyl)dinaphtho[2",3"-1:2'",3'"-q] porphyrazine; zinc (II) 2,9,16-tris-(3-pyridyloxy) tribenzo[b,g,1]-24=(1,1-dimethyl-ethyl)naphtho[2'",3'"-q] porphyrazine; zinc (II) 2,3-bis-(3-pyridyloxy) benzo[b]-10,19,28-tri(1.1-dimethyl-ethyl)trinaphtho[2',3'-g:2",3"1:2'", 3'"-q]porphyrazine; zinc (II) 2,3,18,19-tetrakis-(3-pyridyloxy) dibenzo[b,1]-10,26-di(1,1-dimethyl-ethyl) trinaphtho[2',3'-g:2'",3'"-q]porphyrazine; zinc (II) 2,3,9,10-tetrakis-(3-pyridyloxy) dibenzo[b,g]-17,26-di(1,1-dimethyl-ethyl)dinaphtho[2",3"-1:2'",3'"-q]porphyrazine; zinc (II) 2,3,9,10,16,17-hexakis-(3-pyridyloxy)tribenzo[b,g,1]-24-(1,1-dimethyl-ethyl)naphtho[2'",3'"-q]porphyrazine; zinc (II) 2-(3-N-methyl)pyridyloxy)benzo[b]-10,19,28-tri(1,1-dimethyl-ethyl)trinaphtho[2',3'-g:2",3"1:2'",3'"-q]porphyrazine monoiodide; zinc (II) 2,18-bis-(3-(N-methyl)pyridyloxy) dibenzo[b,1]-10,26-di(1,1-dimethylethyl)dinaphtho[2',3'-g:2'",3'"-q]porphyrazine diiodide; zinc (II) 2,9-bis-(3-(N-methyl)pyridyloxy)dibenzo[b,g]-17,26-di(1,1-dimethylethyl) dinaphtho[2",3"-1:2'",3'"-q]porphyrazine diiodide; zinc (II) 2,9,16-tris-(3-(N-methyl-pyridyloxy)tribenzo[b,g,1]-24-(1,1-dimethylethyl)naphtho[2'",3'"-q]porphyrazine triiodide; zinc (II) 2,3-bis-(3-(N-methyl)pyridyloxy)benzo[b]-10,19,28-tri(1,1-dimethylethyl)trinaphtho[2',3'-g:2",3"-1:2'",3'"-q] porphyrazine diiodide; zinc (II) 2,3,18,19-tetrakis-(3-(N-methyl)pyridyloxy)dibenzo[b,1]-10,26-di(1,1-dimethyl) dinaphtho[2',3'-g:2'",3'"-q]porphyrazine tetraiodide; zinc (II) 2,3,9,10-tetrakis-(3-(N-methyl)pyridyloxy)dibenzo[g,g]-17,26-di(1,1-dimethylethyl)dinaphtho[2",3"-1:2'",3'"-q]porphyrazine tetraiodide; zinc (II) 2,3,9,10,16,17-hexakis-(3-(N-methyl)pyridyloxy)tribenzo[b,g,1]-24-(1,1- dimethylethyl)naphtho[2''',3'''-q]porphyrazine hexaiodide; zinc (II) meso-diphenyl tetrabenzoporphyrin; zinc (II) meso-triphenyl tetrabenzoporphyrin; zinc (II) meso-tetrakis(2,6-dichloro-3-sulfonatophenyl) porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphtaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

Exemplary metallophthalocyanines include aluminum mono-(6-carboxy-pentyl-amino-sulfonyl)-trisulfo-phthalocyanine; aluminum di-(6-carboxy-pentyl-amino-sulfonyl)-trisulfophthalocyanine; aluminum (III) octa-n-butoxy phthalocyanine; aluminum phthalocyanine; aluminum (III) phthalocyanine disulfonate; aluminum phthalocyanine disulfonate; aluminum phthalocyanine disulfonate (cis isomer); aluminum phthalocyanine disulfonate (clinical prep.); aluminum phthalocyanine phthalimido-methyl sulfonate; aluminum phthalocyanine sulfonate; aluminum phthalocyanine trisulfonate; aluminum (III) phthalocyanine trisulfonate; aluminum (III) phthalocyanine tetrasulfonate; aluminum phthalocyanine tetrasulfonate; chloroaluminum phthalocyanine; chloroaluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper (II) tetra-carboxy-phthalocyanine; copper (II)-phthalocyanine; copper t-butyl-phthalocyanine; copper phthalocyanine sulfonate; copper (II) tetrakis-[methylenethio[(dimethyl-amino)methylidyne]]phthalocyanine tetrachloride; dichlorosilicon phthalocyanine; gallium (III) octa-n-butoxy phthalocyanine; gallium (II) phthalocyanine disulfonate; gallium phthalocyanine disulfonate; gallium phthalocyanine tetrasulfonate-chloride; gallium (II) phthalocyanine tetrasulfonate; gallium phthalocyanine trisulfonate-chloride; gallium (II) phthalocyanine trisulfonate; $GaPcS_1tBu_3$; $GaPcS_2tBu_2$; $GaPcS_3tBu_1$; germanium (IV) octa-n-butoxy phthalocyanine; germanium phthalocyanine derivative; silicon phthalocyanine derivative; germanium (IV) phthalocyanine octakis-alkoxy-derivatives; iron phthalocyanine sulfonate; lead (II) 2,3,9,10,16,17,23,24-octakis(3,6-dioxaheptyloxy) phthalocyanine; magnesium t-butyl-phthalocyanine; nickel (II) 2,3,9,10,16,17,23,24-octakis(3,6-dioxaheptyloxy) phthalocyanine; palladium (II) octa-n-butoxy phthalocyanine; palladium (II) tetra(t-butyl)-phthalocyanine; (diol) (t-butyl)$_3$-phthalocyanato palladium (II); ruthenium(II) dipotassium[bis(triphenyl-phosphine-monosulphonate) phthalocyanine; silicon phthalocyanine bis(tri-n-hexyl-siloxy)-; silicon phthalocyanine bis(tri-phenyl-siloxy)-; $HOSiPcOSi(CH_3)_2(CH_2)_3N(CH_3)_2$; $HOSiPcOSi(CH_3)_2(CH_2)_3N(CH_2CH_3)_2$; $SiPc[OSi(CH_3)_2(CH_2)_3N(CH_3)_2]_2$; $SiPc[OSi(CH_3)_2(CH_2)_3N(CH_2CH_3)(CH_2)_2N(CH_3)_2]_2$; tin (IV) octa-n-butoxy phthalocyanine; vanadium phthalocyanine sulfonate; zinc (II) octa-n-butoxy phthalocyanine; zinc (II) 2,3,9,10,16,17,23,24-octakis(2-ethoxy-ethoxy) phthalocyanine; zinc (II) 2,3,9,10,16,17,23,24-octakis(3,6-dioxaheptyloxy) phthalocyanine; zinc (II) 1,4,8,11,15,18,22,25-octa-n-butoxy-phthalocyanine; zn(II)-phthalocyanine-octabutoxy; zn(II)-phthalocyanine; zinc phthalocyanine; zinc (II) phthalocyanine; zinc phthalocyanine and perdeuterated zinc phthalocyanine; zinc (II) phthalocyanine disulfonate; zinc phthalocyanine disulfonate; zinc phthalocyanine sulfonate; zinc phthalocyanine tetrabromo-; zinc (II) phthalocyanine tetra-t-butyl-; zinc (II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc ((I) tetrakis-(1,1-dimethyl-2-phthalimido)ethyl phthalocyanine; zinc (II) tetrakis-(1,1-dimethyl-2-amino)-ethyl-phthalocyanine; zinc (II) phthalocyanine tetrakis(1,1-dimethyl-2-trimethyl ammonium)ethyl tetraiodide; zinc phthalocyanine tetrasulphonate; zinc phthalocyanine tetrasulfonate; zinc (II) phthalocyanine tetrasulfonate; zinc (II) phthalocyanine trisulfonate; zinc phthalocyanine trisulfonate; zinc (II) (t-butyl)$_3$-phthalocyanine diol; zinc tetradibenzobarreleno-octabutoxy-phthalocyanine; zinc (II) 2,9,16,23,-tetrakis-(3-(N-methyl)pyridyloxy)phthalocyanine tetraiodide; and zinc (II) 2,3,9,10,16,17,23,24-octakis-(3-(N-methyl)pyridyloxy)phthalocyanine complex octaiodide; and zinc (II) 2,3,9,10,16,17,23,24-octakis-(3-pyridyloxy)phthalocyanine.

Exemplary methylene blue derivatives include 1-methyl methylene blue; 1,9-dimethyl methylene blue; methylene blue; methylene blue (16 μM); methylene blue (14 μM); methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N'-bis-(hydroperoxy-2-methoxyethyl)-1,4,5,8-naphthaldiimide; N-(hydroperoxy-2-methoxyethyl)-1,8-naphthalimide; 1,8-naphthalimide; N,N'-bis(2,2-dimethoxyethyl)-1,4,5,8-naphthaldiimide; and N,N'-bis(2,2-dimethylpropyl)-1,4,5,8-naphthaldiimide.

Exemplary naphthalocyanines include aluminum t-butyl-chloronaphthalocyanine; silicon bis(dimethyloctadecylsiloxy) 2,3-naphthalocyanine; silicon bis(dimethyloctadecylsiloxy) naphthalocyanine; silicon bis(dimethylthexylsiloxy) 2,3-naphthalocyanine; silicon bis(dimethylthexylsiloxy) naphthalocyanine; silicon bis(t-butyldimethylsiloxy) 2,3-naphthalocyanine; silicon bis(tert-butyldimethylsiloxy) naphthalocyanine; silicon bis(tri-n-hexylsiloxy) 2,3-naphthalocyanine; silicon bis(tri-n-hexylsiloxy) naphthalocyanine; silicon naphthalocyanine; t-butylnaphthalocyanine; zinc (II) naphthalocyanine; zinc (II) tetraacetyl-amidonaphthalocyanine; zinc (II) tetraminonaphthalocyanine; zinc (II) tetrabenzamidonaphthalocyanine; zinc (II) tetrahexylamidonaphthalocyanine; zinc (II) tetramethoxy-benzamidonaphthalocyanine; zinc (II) tetramethoxynaphthalocyanine; zinc naphthalocyanine tetrasulfonate; and zinc (II) tetradodecylamidonaphthalocyanine.

Exemplary nile blue derivatives include benzo[a]phenothiazinium, 5-amino-9-diethylamino-; benzo[a]phenothiazinium, 5-amino-9-diethylamino-6-iodo-; benzo[a]phenothiazinium, 5-benzylamino-9-diethylamino-; benzo[a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[a]phenoxazinium, 5-amino-9-diethylamino-2,-iodo; benzo[a]phenoxazinium, 5-amino-9-diethylamino-6-iodo-; benzo[a]phenoxazinium, 5-benzylamino-9-diethylamino-(nile blue 2B); 5-ethylamino-9-diethylamino-benzo[a]phenoselenazinium chloride; 5-ethylamino-9-diethyl-aminobenzo[a]phenothiazinium chloride; and 5-ethylamino-9-diethyl-aminobenzo[a]phenoxazinium chloride.

Exemplary NSAIDs (nonsteroidal anti-inflammatory drugs) include benoxaprofen; carprofen; carprofen dechlorinated (2-(2-carbazolyl) propionic acid); carprofen (3-chlorocarbazole); chlorobenoxaprofen; 2,4-dichlorobenoxaprofen;

cinoxacin; ciprofloxacin; decarboxy-ketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomelfloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam ; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A; acetoxy hypocrellin B; acetoxy iso-hypocrellin A; acetoxy iso-hypocrellin B; 3,10-bis[2-(2-aminoethylamino)ethanol] hypocrellin B; 3,10-bis[2-(2-aminoethoxy)ethanol] hypocrellin B; 3,10-bis[4-(2-aminoethyl)morpholine] hypocrellin B; n-butylaminated hypocrellin B; 3,10-bis(butylamine) hypocrellin B; 4,9-bis(butylamine) hypocrellin B; carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo[1,12-CBr=CMeCBr(COMe)] hypocrellin B; 5,8-dibromo[1,12-CHBrC(=CH$_2$)CBr(COMe)] hypocrellin B; 5,8-dibromo[1-CH$_2$COMe, 12-COCOCH$_2$Br-] hypocrellin B; 5,8-dichloro hypocrellin A; 5,8-dichloro hypocrellin B; 5,8-dichlorodeacytylated hypocrellin B; 5,8-diiodo hypocrellin A; 5,8-diiodo hypocrellin B; 5,8-diiodo[1,12-CH=CMeCH(COCH$_2$I$_2$)-] hypocrellin B; 5,8-diiodo[1,12-CH$_2$C(CH$_2$I)=C(COMe)-] hypocrellin B; 2-(N,N-diethylamino) ethylaminated hypocrellin B; 3,10-bis[2-(N,N-diethylamino)-ethylamine]hypocrellin B; 4,9-bis[2-(N,N-diethylamino)-ethylamine] iso-hypocrellin B; dihydro-1,4-thiazine carboxylic acid hypocrellin B; dihydro-1,4-thiazine hypocrellin B; 2-(N,N-dimethylamino) propylamine hypocrellin B; dimethyl-1,3,5,8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 11-hydroxy hypocrellin B or 2-hydroxy hypocrellin B; hypocrellin A; hypocrellin B; 5-iodo[1,12-CH$_2$C(CH$_2$I)=C(COMe)-] hypocrellin B; 8-iodo[1,12-CH$_2$C(CH$_2$I)=C(COMe)—] hypocrellin B; 9-methylamino iso-hypocrellin B; 3,10-bis[2-(N,N-methylamino)propylamine]hypocrellin B; 4,9-bis(methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8,15-tribromo hypocrellin B; calphostin C, Cercosporins such as acetoxy cercosporin; acetoxy iso-cercosporin; aminocercosporin; cercosporin; cercosporin+iso-cercosporin (1/1 molar); diaminocercosporin; dimethylcercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl 13$^1$-deoxy-20-formyl-7,8-vic-dihydro-bacterio-meso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether (ester); dihematoporphyrin ether; dihematoporphyrin ether (ester)-chlorin; hematoporphyrin-chlorin ester; hematoporphyrin-low density lipoprotein conjugate; hematoporphyrin-high density lipoprotein conjugate; porphine-2,7,18-tripropanoic acid, 13,13'-(1,3-propanediyl)bis[3,8,12,17-tetramethyl]-; porphine-2,7,18-tripropanoic acid, 13,13'-(1,11-undecanediyl)bis[3,8,12,17-tetramethyl]-; porphine-2,7,18-tripropanoic acid, 13,13'-(1,6-hexanediyl)bis[3,8,12,17-tetramethyl]-; SnCe6-MAb conjugate 1.7:1; SnCe6-MAb conjugate 1.7:1; SnCe6-MAb conjugate 6.8:1; SnCe6-MAb conjugate 11.2:1; SnCe6-MAb conjugate 18.9:1; SnCe6-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate (12:1); α-terthienyl-bovine serum albumin conjugate (4:1); and tetraphenylporphine linked to 7-chloroquinoline.

Exemplary phthalocyanines include (diol) (t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24-octakis2-ethoxyethoxy) phthalocyanine; 2,3,9,10,16,17,23, 24-octakis(3,6-dioxaheptyloxy) phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-(2$^3$-carboxy-2$^4$-methoxycarbonyl benzo)-7,12,17-tris(2-methoxyethyl) porphycene; 2-(2-hydroxyethyl)-7,12,17-tri(2-methoxyethyl) porphycene; 2-(2-hydroxyethyl)-7,12,17-tri-n-propyl-porphycene; 2-(2-methoxyethyl)-7,12,17-tri-n-propyl-porphycene; 2,7,12,17-tetrakis(2-methoxyethyl) porphycene; 2,7,12,17-tetrakis(2-methoxyethyl)-9-hydroxy-porphycene; 2,7,12,17-tetrakis(2-methoxyethyl)-9-methoxy-porphycene; 2,7,12,17-tetrakis(2-methoxyethyl)-9-n-hexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis(2-methoxyethyl)-9-pelargonyloxy-porphycene; 2,7,12,17-tetrakis(2-methoxyethyl)-9-stearoyloxy-porphycene; 2,7,12,17-tetrakis(2-methoxyethyl)-9-(N-t-butoxycarbonylglycinoxy) porphycene; 2,7,12,17-tetrakis(2-methoxyethyl)-9-[4-((β-apo-7-carotenyl)benzoyloxyl-porphycene; 2,7,12,17-tetrakis(2-methoxyethyl)-9-amino-porphycene; 2,7,12,17-tetrakis(2-methoxyethyl)-9-acetamido-porphycene; 2,7,12,17-tetrakis(2-methoxyethyl)-9-glutaramido-porphycene; 2,7,12,17-tetrakis(2-methoxyethyl)-9-(methyl-glutaramido)-porphycene; 2,7,12,17-tetrakis(2-methoxyethyl)-9-

(glutarimido)-porphycene; 2,7,12,17-tetrakis(2-methoxyethyl)-3-(N,N-dimethylaminomethyl)-porphycene; 2,7,12,17-tetrakis(2-methoxyethyl)-3-(N,N-dimethylaminomethyl)-porphycene hydrochloride; 2,7,12,17-tetrakis(2-ethoxyethyl)-porphycene; 2,7,12,17-tetra-n-propyl-porphycene; 2,7,12,17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t-butoxycarbonylglycinoxy)-porphycene; 2,7,12,17-tetra-n-propyl-9-(4-N-t-butoxy-carbonyl-butyroxy)-porphycene; 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutaramido)-porphycene; 2,7,12,17-tetra-n-propyl-3-(N,N-dimethylaminomethyl) porphycene; 2,7,12,17-tetra-n-propyl-9,10-benzo porphycene; 2,7,12,17-tetra-n-propyl-9-p-benzoyl carboxy-porphycene; 2,7,12,17-tetra-n-propyl-porphycene; 2,7,12,17-tetra-t-butyl-3,6;13,16-dibenzo-porphycene; 2,7-bis(2-hydroxyethyl)-12,17-di-n-propyl-porphycene; 2,7-bis(2-methoxyethyl)-12,17-di-n-propyl-porphycene; and porphycene.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin (8 μM); hematoporphyrin (400 μM); hematoporphyrin (3 μM); hematoporphyrin (18 μM); hematoporphyrin (30 μM); hematoporphyrin (67 μM); hematoporphyrin (150 μM); hematoporphyrin IX; hematoporphyrin monomer; hematoporphyrin dimer; hematoporphyrin derivative; hematoporphyrin derivative (6 μM); hematoporphyrin derivative (200 μM); hematoporphyrin derivative A (20 μM); hematoporphyrin IX dihydrochloride; hematoporphyrin dihydrochloride; hematoporphyrin IX dimethylester; haematoporphyrin IX dimethylester; mesoporphyrin dimethylester; mesoporphyrin IX dimethylester; monoformyl-monovinyl-deuteroporphyrin IX dimethylester; monohydroxyethylvinyl deuteroporphyrin; 5,10,15,20-tetra(o-hydroxyphenyl) porphyrin; 5,10,15,20-tetra(m-hydroxyphenyl) porphyrin; 5,10,15,20-tetrakis-(m-hydroxyphenyl) porphyrin; 5,10,15,20-tetra(p-hydroxyphenyl) porphyrin; 5,10,15,20-tetrakis (3-methoxyphenyl) porphyrin; 5,10,15,20-tetrakis (3,4-dimethoxyphenyl) porphyrin; 5,10,15,20-tetrakis (3,5-dimethoxyphenyl) porphyrin; 5,10,15,20-tetrakis (3,4,5-trimethoxyphenyl) porphyrin; 2,3,7,8,12,13,17,18-octaethyl-5,10,15,20-tetraphenylporphyrin; Photofrin®; Photofrin® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylamino-formamide; protoporphyrin formamide; sapphyrin 1 3,12,13,22-tetraethyl-2,7,18,23 tetramethyl sapphyrin-8,17-dipropanol; sapphyrin 2 3,12,13,22-tetraethyl-2,7,18,23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl) porphine; meso-tetra-(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium) porphine; meso-tetra-(4-N,N,N"trimethylamino-phenyl) porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl)porphine; tetra(4-sulfonatophenyl)porphine; tetraphenylporphyrin sulfonate; meso-tetra(4-sulfonatophenyl)porphine; tetrakis (4-sulfonatophenyl)porphyrin; meso-tetra(4-sulfonatophenyl)porphine; meso(4-sulfonatophenyl)porphine; meso-tetra(4-sulfonatophenyl)porphine; tetrakis(4-sulfonatophenyl) porphyrin; meso-tetra(4-N-trimethylanilinium)-porphine; uroporphyrin; uroporphyrin I (17 μM); uroporphyrin IX; and uroporphyrin I (18 μM).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudopsoralen; 5',7-dimethyl-isopseudopsoralen; pseudoisopsoralen; 3-acetopseudoisopsoralen; 3/4',5'-trimethyl-aza-psoralen; 4,4',8-trimethyl-5'-amino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxy-psoralen; 5'-acetyl-4,8-dimethyl-psoralen; 5'-aceto-8-methyl-psoralen; and 5'-aceto-4,8-dimethyl-psoralen Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include 1-amino-4,5-dimethoxy anthraquinone; 1,5-diamino-4,8-dimethoxy anthraquinone; 1,8-diamino-4,5-dimethoxy anthraquinone; 2,5-diamino-1,8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chlorohydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2':5',2"-terthiophene; 2,2':5',2"-terthiophene-5-carboxamide; 2,2':5',2"-terthiophene-5-carboxylic acid; 2,2':5',2"-terthiophene-5-L-serine ethyl ester; 2,2':5',2"-terthiophene-5-N-isopropynyl-formamide; 5-acetoxymethyl-2,2':5',2"-terthiophene; 5-benzyl-2,2':5',2"-terthiophene-sulphide; 5-benzyl-2,2':5',2"-terthiophene-sulfoxide; 5-benzyl-2,2':5',2"-terthiophene-sulphone; 5-bromo-2,2':5',2"-terthiophene;

5-(butynyl-3'''-hydroxy)-2,2':5',2''-terthiophene; 5-carboxyl-5''-trimethylsilyl-2,2':5',2''-terthiophene; 5-cyano-2,2':5',2''-terthiophene; 5,5''-dibromo-2,2':5',2''-terthiophene; 5-(1''', 1'''-dibromoethenyl)-2,2':5',2''-terthiophene; 5,5''-dicyano-2, 2':5',2''-terthiophene; 5,5''-diformyl-2,2':5',2''-terthiophene; 5-difluoromethyl-2,2':5',2''-terthiophene; 5,5''-diiodo-2,2':5', 2''-terthiophene; 3,3''-dimethyl-2,2':5',2''-terthiophene; 5,5''-dimethyl-2,2':5',2''-terthiophene; 5-(3''',3'''-dimethylacryloyloxymethyl)-2,2':5',2''-terthiophene; 5,5''-di-(t-butyl)-2,2':5', 2''-terthiophene; 5,5''-dithiomethyl-2,2':5',2''-terthiophene; 3'-ethoxy-2,2':5',2''-terthiophene; ethyl 2,2':5',2''-terthiophene-5-carboxylic acid; 5-formyl-2,2':5',2''-terthiophene; 5-hydroxyethyl-2,2':5',2''-terthiophene; 5-hydroxymethyl-2,2':5',2''-terthiophene; 5-iodo-2,2':5',2''-terthiophene; 5-methoxy-2,2':5',2''-terthiophene; 3'-methoxy-2,2':5',2''-terthiophene; 5-methyl-2,2':5',2''-terthiophene; 5-(3'''-methyl-2'''-butenyl)-2,2':5',2''-terthiophene; methyl 2,2':5',2''-terthiophene-5-[3'''-acrylate]; methyl 2,2':5',2''-terthiophene-5-(3'''-propionate); N-allyl-2, 2':5',2''-terthiophene-5-sulphonamide; N-benzyl-2,2':5',2''-terthiophene-5-sulphonamide; N-butyl-2,2':5',2''-terthiophene-5-sulphonamide; N,N-diethyl-2,2':5',2''-terthiophene-5-sulphonamide; 3,3',4',3''-tetramethyl-2,2':5', 2''-terthiophene; 5-t-butyl-5''-trimethylsilyl-2,2':5',2''-terthiophene; 3'-thiomethyl-2,2':5',2''-terthiophene; 5-thiomethyl-2,2':5',2''-terthiophene; 5-trimethylsilyl-2,2':5', 2''-terthiophene, bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4''-hydroxy)-2,2'-bithiophene; 5-(pentynyl-5''-hydroxy)-2,2'-bithiophene; 5-(3'',4''-dihydroxybutynyl)-2, 2'-bithiophene derivative; 5-(ethoxybutynyl)-2,2'-bithiophene derivative, and misclaneous thiophenes such as 2,5-diphenylthiophene; 2,5-di(2-thienyl)furan; pyridine,2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene) bis-; thiophene, 2,2'-(1,4-phenylene)bis-; 2,2':5',2'':5'',2'''-quaterthiophene; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester; and zinc methylpyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include Eosin B (4',5'-dibromo, 2',7'-dinitro-fluorescein, dianion); eosin Y; eosin Y (2',4',5', 7'-tetrabromo-fluorescein, dianion); eosin (2',4',5',7'-tetrabromo-fluorescein, dianion); eosin (2',4',5',7'-tetrabromofluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2', 7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythrosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); rose bengal; rose bengal dianion; rose bengal O-methyl-methylester; rose bengal 6'-O-acetyl ethyl ester; rose bengal benzyl ester diphenyl-diiodonium salt; rose bengal benzyl ester triethylammonium salt; rose bengal benzyl ester, 2,4,6,-triphenylpyrilium salt; rose bengal benzyl ester, benzyltriphenylphosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammonium salt; rose bengal benzyl ester, triphenyl pyrilium; rose bengal bis (triethyl-ammonium) salt) (3,4,5,6-tetrachloro-2',4',5',7'-tetraiodofluorescein, bis (triethyl-ammonium salt); rose bengal bis (triethyl-ammonium) salt; rose bengal bis(benzyl-triphenyl-phosphonium) salt (3,4,5,6-tetrachloro-2',4',5',7'-tetraiodofluorescein, bis(benzyl-triphenyl-phosphonium) salt); rose bengal bis(diphenyl-iodonium) salt (3,4,5,6-tetrachloro-2',4',5',7'-tetraiodofluorescein, bis(diphenyl-iodonium) salt); rose bengal di-cetyl-pyridinium chloride ion pair; rose bengal ethyl ester triethyl ammonium salt; rose bengal ethyl ester triethyl ammonium salt; rose bengal ethyl ester; rose bengal methyl ester; rose bengal octyl ester tri-n-butyl-ammonium salt RB; rose bengal, 6'-O-acetyl-, and ethyl ester.

Any of the photoactive compounds described above can be used in the method of the invention; of course, mixtures of two or more photoactive compounds can also be used; however, the effectiveness of the treatment depends on the absorption of light by the photoactive compound so that if mixtures are used, components with similar absorption maxima are preferred. Alternatively, and if the invention is practiced with light of a broader range of wavelengths or of discrete (or non-overlapping wavelengths), combinations of photoactive compounds with absorption spectra corresponding to wavelengths within the broader range or within the wavelengths present may be used.

Formulations

The photoactive agent is formulated so as to provide an effective concentration to the target ocular tissue. The photoactive agent may be coupled to a specific binding ligand which may bind to a specific surface component of the target ocular tissue or, if desired, by formulation with a carrier that delivers higher concentrations to the target tissue. The formulation may be a liposomal formulation, an emulsion, or simply an aqueous solution. Buffers and other excipients may also be added. Gelling agents and other excipients may also be employed. The nature of the formulation will depend in part on the mode of administration and on the nature of the photoactive agent selected. To prepare a pharmaceutical formulation or composition comprising a PS of the invention, any pharmaceutically acceptable excipient, or combination thereof, appropriate to the particular photoactive compound may be used. Thus, the photoactive compound may be administered as an aqueous composition, as a transmucosal or transdermal composition, or in an oral formulation. The formulation may also include liposomes. Liposomal compositions are particularly preferred especially where the photoactive agent is a green porphyrin. Liposomal formulations are believed to deliver the green porphyrin selectively to the low-density lipoprotein component of plasma which, in turn acts as a carrier to deliver the active ingredient more effectively to the desired site. Increased numbers of LDL receptors have been shown to be associated with neovascularization, and by increasing the partitioning of the green porphyrin into the lipoprotein phase of the blood, it appears to be delivered more efficiently to neovasculature.

As previously mentioned, the method of the invention is particularly effective where the loss of visual acuity in the patient is associated with unwanted neovasculature. Green porphyrins, and in particular BPD-MA, strongly interact with such lipoproteins. LDL itself can be used as a carrier, but LDL is considerably more expensive and less practical than a liposomal formulation. LDL, or preferably liposomes, are thus preferred carriers for the green porphyrins since green porphyrins strongly interact with lipoproteins and are easily packaged in liposomes. Compositions of green porphyrins involving lipocomplexes, including liposomes, are described in U.S. Pat. No. 5,214,036 and in U.S. Pat. No. 6,074,666, the disclosures of both of these being incorporated herein by reference. Liposomal BPD-MA for intravenous administration can also be obtained from QLT Inc., Vancouver, British Columbia.

Administration and Dosage

The photoactive compound can be administered in any of a wide variety of ways, for example, orally, parenterally, or rectally, or the compound may be placed directly in the eye. Parenteral administration, such as intravenous, intramuscular, or subcutaneous, is preferred. Intravenous injection or infusion are especially preferred. Localized administration, including topical administration, may also be used.

The dose of photoactive compound can vary widely depending on the mode of administration; the formulation in which it is carried, such as in the form of liposomes; or whether it is coupled to a target-specific ligand, such as an antibody or an immunologically active fragment. As is generally recognized, there is a nexus between the type of photoactive agent, the formulation, the mode of administration, and the dosage level. Adjustment of these parameters to fit a particular combination is possible.

Additionally, the PS concentration in the formulation to be administered will depend on the nature of the tissue to be treated, the manner in which the formulation is administered, and the nature of the PS. Typical concentrations, however, are in the range of about 1 ng/ml to about 10 µg/ml, preferably about 2 ng/ml to about 1 µg/ml, and typically in the range of about 10 ng/ml to about 100 ng/ml. However, these values are merely suggestions and may not apply to all PSs.

While various photoactive compounds require different dosage ranges, if green porphyrin's are used, a typical dosage is of the range of 0.1-50 mg/M$^2$ (of body surface area) preferably from about 1-10 mg/M$^2$ and even more preferably about 2-8 mg/M$^2$, and most preferably about 6 mg/M$^2$. If verteporfin is the photoactive agent, it is preferably used at about 6 mg/M$^2$. However, these values are merely suggestions and may not apply to all photosensitizers. 6 mg/m$^2$ is approximately 0.15 mg/kg.

Systemic administration can also be stated in terms of amount of PS to body weight of the subject being treated. Dosages for this invention stated in such terms are less than about 10 µg/kg to 100 mg/kg body weight, preferably less than about 10 mg/kg, more preferably about 0.15 mg/kg in humans. Preferably, the PS is infused into a subject over a short period, such as, but not limited to, about 5 to about 120 minutes, about 10 to about 90 minutes, about 20 to about 60 minutes, or about 30 to 45 minutes. Particularly preferred is an infusion over 10 minutes.

The various parameters used for effective, selective photodynamic therapy in the invention are interrelated. Therefore, the dose should also be adjusted with respect to other parameters, for example, fluence, irradiance, duration of the light used in photodynamic therapy, and time interval between administration of the dose and the therapeutic irradiation. All of these parameters should be adjusted to produce significant enhancement of visual acuity without significant damage to the eye tissue.

Stated in alternative terms, as the photoactive compound dose is reduced, the fluence required to close choroidal neovascular tissue tends to increase.

Light Treatment

After the photoactive compound or PS has been administered, the target ocular tissue is irradiated at the wavelength absorbed by the agent selected. The spectra for the photoactive compounds described above, as well as wavelengths required for PS activation are known in the art. Irradiation of the administered PS is preferably at the wavelength(s) absorbed by the compound selected. For any particular photoactive compound, it is a trivial matter to ascertain the spectrum. For green porphyrins, however, the desired wavelength range is generally between about 550 and 695 nm. A wavelength in this range is especially preferred for enhanced penetration into bodily tissues. Preferred wavelengths for the practice of the invention are at about 685-695 nm, particularly at about 686, about 687, about 688, about 689, about 690, about 691, and about 692 nm.

Photoactive compound (photosensitizer or PS) spectra, as well as wavelengths for their activation, have been described in the art. Irradiation of the administered photosensitizer is preferably at the wavelength absorbed by the photosensitizer selected.

As a result of being irradiated, the photoactive compound in its excited state is thought to interact with other compounds to form reactive intermediates, such as singlet oxygen, which can cause disruption of cellular structures. Possible cellular targets include the cell membrane, mitochondria, lysosomal membranes, and the nucleus. Evidence from tumor and neovascular models indicates that occlusion of the vasculature is a major mechanism of photodynamic therapy, which occurs by damage to endothelial cells, with subsequent platelet adhesion, degranulation, and thrombus formation.

The fluence during the irradiating treatment can vary widely, depending on type of tissue, depth of target tissue, and the amount of overlying fluid or blood, but preferably varies from about 20-200 Joules/cm$^2$. The irradiation levels will be in the range generally employed for PDT treatment of CNV as known in the art. Typical levels for the practice of the invention are in the range of about 12.5, 25, 50, 75, and 100 J/cm$^2$. The radiation can be supplied by any convenient source using a wavelength absorbed by the photosensitizer used. Examples of sources for use in the present methods include, but are not limited to, any assembly capable of producing visible light.

The total PDT dose depends on the balance of at least the concentration of PS employed, light intensity (fluence rate), and time of irradiation which determines total energy. The values set forth hereinbelow for these parameters indicates the range in which they may be varied; however, equivalents of the following are known to the skilled practitioner and are also within the scope of the invention.

The irradiance typically varies from about 150-900 mW/cm$^2$, with the range between about 150-600 mW/cm$^2$ being preferred. However, the use of higher irradiances may be selected as effective and having the advantage of shortening treatment times. With verteporfin PDT, irradiances in the range of 300-600 mW/cm$^2$ are preferred. Preferred rates for use with green porphyrins or BPDs in general are from about 200 to 250, about 250 to 300, about 300 to 350, about 350 to 400, about 400 to 450, about 450 to 500, and about 500 to 550 mW/cm$^2$.

It is understood that the selection of particular fluence rates will vary according to the nature of the neovasculature and tissue being treated and the nature of the PS employed. However, the conditions for PDT (including PS concentration, fluence rate, and time of irradiation) cannot vary over any arbitrary range. There are actual constraints which are known by the skilled practitioner with the use of any PS in PDT.

As used herein "electromagnetic radiation," unless otherwise indicated, is meant generally to refer to the visible light range of the electromagnetic spectrum, generally including wavelengths between 400 nm and 700 nm. The terms "visible light" and "visible light radiation" and variations thereof are meant to be encompassed within the scope of the term "electromagnetic radiation." In addition, this term may also be used herein to refer to electromagnetic radiation within the ultraviolet (including wavelengths below 400 nm) and infrared spectra (including wavelengths above 700 nm).

The optimum time following photoactive agent administration until light treatment can also vary widely depending on the mode of administration and the form of administration and the specific ocular tissue or condition being targeted. Typical times after administration of the photoactive agent range from about 1 minute to about 3 hours after the start of the infusion of the photoactive compound, preferably about 10-45 minutes, and more preferably 15-30 minutes. Fifteen minutes after the start of a 10 minute infusion has been shown to be effective in the use of verteporfin PDT to treat predominantly classic CNV. With occult CNV, delayed light treatment, which is longer than 15 minutes, but less than about 45 minutes may be preferred. Preferably, irradiation is provided between about 15 and about 30 minutes after the start of a 10 minute infusion of verteporfin when treating occult lesions. In a particularly preferred embodiment, light is administered 30 minutes after the start of a 10 minute infusion of verteporfin. The incubation before irradiation may occur in the dark or low-level light may be supplied during PS administration.

The duration of light irradiation depends on the fluence desired; for an irradiance of 600 mW/cm$^2$ a fluence of 50 J/cm$^2$ requires 83 seconds of irradiation; 150 J/cm$^2$ requires 249 seconds of irradiation. With verteporfin PDT, a fluence of between 30 and 50 J/cm$^2$ is preferred.

Evaluation of Treatment

Clinical examination and fundus photography typically reveal no color change immediately following photodynamic therapy, although a mild retinal whitening occurs in some cases after about 24 hours. In general, effects of the photodynamic therapy as regards reduction of neovascularization can be performed using standard fluorescein angiographic techniques at specified periods after treatment. Parameters that are monitored in AMD patients or subjects include the progression from baseline of classic CNV in the lesion, progression from baseline of occult CNV in the lesion, change from baseline in greatest linear dimension of the entire CNV lesion, change from baseline in area of the entire lesion including CNV, natural scar and obscuring features (measured in Macular Photocoagulation Study Disc Area, MPS DA), and change from baseline in area of the entire lesion plus surrounding atrophy (measured in MPS DA).

Efficacy of PDT treatment is measured primarily by evaluation of visual acuity following treatment. This is done using means similar to that described above. Parameters that are typically monitored in evaluation of a treatment protocol are gain or loss of letters from baseline (e.g. percent of subjects gaining/losing 15 letters or more, percent of subjects losing 30 letters or more, best-corrected visual acuity decreasing less than 34 letters, etc.), the time it takes to lose letters (e.g. time to lose 15 or more letters, time to lose 30 or more letters) and absolute changes from baseline visual acuity scores.

Frequency of Treatment.

After the initial PDT treatment, an angiographic examination is carried out to determine if neovascular leakage has recurred. If upon angiographic evaluation, it is apparent that neovascular leakage is recurring, the subject can be retreated. The following examples are to illustrate but not to limit the invention.

EXAMPLE 1

Assessment of Visual Acuity

1. Visual Acuity Equipment and Facilities

The visual acuity of subjects are measured based on the procedure developed for the Early Treatment Diabetic Retinopathy Study (ETDRS). The following equipment is used:

a set of three Lighthouse Distance Visual Acuity Test charts (modified ETDRS Charts 1, 2, and R), retroilluminated box providing standardized chart illumination. The charts and boxes are manufactured by and can be obtained from Lighthouse Low Vision Products, 36-02 Northern Boulevard, Long Island, N.Y., Tel.: (718) 937-6959;

visual acuity charts with charts 1 and 2 used for testing the right and left eye, respectively, and chart R or a Snellen chart used for refraction;

visual acuity box;

retroilluminated box;

visual acuity lanes using exact distances between the patient's eyes and wall mounted or stand mounted boxes; and refraction technique performed by a certified visual acuity examiner.

Other equipment required for refraction are Retroilluminated Chart R from the ETDRS (modified Bailey-Lovie chart) visual acuity chart set; trial lens frames; wire-rimmed lens set, with positive or negative cylinder lenses; +0.37 and −0.37 spherical lenses; Jackson cross-cylinders of 0.25, 0.5, and 1.00 diopters; pinhole occluder and tissues.

At the initial visit, the subject's present glasses (spectacles) for distance viewing (if worn) may be measured with a lensometer, and these measurements used as the beginning approximate refraction. Refractions may be performed with positive or negative cylinder power. Each center must designate positive or negative cylinder and must use the same designation throughout the study. If the subject does not wear glasses for distance vision, retinoscopy or autorefraction may be performed. When no correction is given by any method, the beginning approximate refraction should be no lens correction or piano. The best correction determined from subjective refraction at each visit should be recorded on the Record of Subjective Refraction maintained for each subject. At each follow-up visit, the refraction recorded at the previous visit should be used as the beginning approximate refraction for each eye. Only at the baseline examination should the distance prescription worn in glasses be used.

Each eye should be refracted at 2 meters unless the visual acuity measured at this distance on the chart used for refraction (Chart R) is worse than 20/320. When visual acuity is worse than 20/320, the eye is refracted at 1 meter with a +2.00 and −2.00 sphere only. Whenever a subject cannot read any letters on the top line of Chart R at 1 meter with the non-study eye with the beginning approximate refraction, the vision should be checked with a pinhole to see whether reduced vision is due, at least in part, to larger refractive error. If there is no improvement with pinhole, the non-study eye is exempt from refraction. However, the visual acuity of the non-study eye may be measured and recorded in the usual way, beginning at 2 meters first, with the beginning approximate refractive correction.

Subjects who arrive for examination wearing contact lenses may be refracted over their lenses starting with plano. The lens correction recorded may be the final correction in the trial frame at the end of refraction and spherical refinement in the visual acuity lane. Corrected aphakic subjects, including those with intraocular lenses, may undergo subjective refraction as specified below. For uncorrected aphakic subjects, a +10.00 diopter sphere may be added to the trial frame as the beginning approximate refraction.

should

A summary of a refractive protocol is provided in Table 1 below.

TABLE 1

Refraction Protocol Summary

| Vision with Best Correction | Sphere | | Cylinder | | | Sphere Refinement | |
|---|---|---|---|---|---|---|---|
| (Refraction Distance) | Power (a) | Increment | Axis (b) | Power (c) | Increment | Power (d) | Increment |
| 20/20-20/80 (2 meters) | +.50 −.37 +.50 | +.50 −.25 +.50 | .50 JCC | .25 JCC | +.25 −.25 | +.37 −.37 +.37 | +.25 −.25 +.25 |
| <20/80-20/160 (2 meters) | +1.00 −1.00 +1.00 | +1.00 −1.00 +1.00 | 1.00 JCC | 1.00 JCC | +1.00 −1.00 | +.50 −.50 +.50 | +.50 −.50 +.50 |
| 20/200-20/320 (2 meters) | +2.00 −2.00 +2.00 | +2.00 −2.00 +2.00 | 1.00 JCC | 1.00 JCC | +1.00 −1.00 | +1.00 −1.00 +1.00 | +1.00 −1.00 +1.00 |
| <20/320 (1 meter) | +2.00 −2.00 | +2.00 −2.00 | No cylinder test | | | No refinement | |

The sequence of refraction and testing for best-corrected visual acuity have been set forth in U.S. Provisional Application 60/266,940, filed Feb. 6, 2001, which has been incorporated by reference as if fully set forth.

Scoring Best-Corrected Visual Acuity may be conducted as follows: the examiner records each letter identified correctly by circling the corresponding letter on the Visual Acuity Worksheet. Letters read incorrectly are marked with an "X" and letters for which no guesses are made are not marked on the form. Each letter read correctly is scored as one point. The score for each line (which is zero if no letters are read correctly) and the total score for each eye are recorded after testing is completed. If testing at 1 meter is not required, 15 points are automatically scored for the 1-meter test. The total combined score (i.e., the sum of the 2- and 1-meter scores) and the approximate Snellen fraction, which is determined based on the lowest line read with one or fewer mistakes, are recorded on the Visual Acuity Worksheet.

EXAMPLE 2

Assessment of Lesions and Measurement of Lesion Size

Baseline fundus photographs and fluorescein angiograms taken of subjects are evaluated to confirm fundus features and to describe baseline features of the choroidal neovascular lesions that are likely to affect the visual outcome.

Fundus photographs and fluorescein angiograms are obtained at a screening visit, within 7 days prior to randomization. Fundus photographs and fluorescein angiograms are obtained at follow-up visits every three months thereafter for a period of up to two years.

Fundus cameras of 30° or 35° field with magnification within the range of 2.4× to 2.6× are recommended for the study. The Zeiss 30° camera is most preferred camera because of the superior quality of the image when compared to the other available cameras. A 45° camera is acceptable according to the protocol, as long as the magnification is still within the acceptable range of 2.4× to 2.6×. Cameras with fields of 25° or 60° are not acceptable.

Disc Area Template

The WILMER READING CENTER template of MPS Disc Area Circles labeled for the Zeiss 30° camera dated 10/96 were used to determine the area of on fluorescein angiograms from any of the cameras identified above. It also is used to determine the size category for the greatest linear dimension of the lesion to be treated.

Reticle

Included on the disc area template is a millimeter scale (reticle) which is used by the treating ophthalmologist directly on the angiogram to measure the greatest linear dimension of the lesion to be treated. This reticle has been used to measure the greatest linear dimension of the MPS Disc Area Template circles and create a conversion table found in Table 1.

Conversion Table (Reticle Measurement of MPS Disc Area Circles)

To compare the treating ophthalmologist's measurement of the greatest linear dimension of the lesion to the readers' assessment of the greatest linear dimension the following table has been constructed to illustrate the size range in millimeters of each MPS disc area circle category.

| DA Circle | Diameter on the Template (mm) | Diameter in the Eye 1 (mm) | Area in the Eye (mm2) |
|---|---|---|---|
| 1 | 4.5 | 1.80 | 2.54 |
| 2 | 6.3 | 2.52 | 4.99 |
| 3 | 7.9 | 3.16 | 7.84 |
| 3.5 | 8.3 | 3.32 | 8.65 |
| 4 | 8.9 | 3.56 | 9.95 |
| 5 | 10.2 | 4.08 | 13.07 |
| 6 | 11.3 | 4.52 | 16.04 |
| 9 | 14.0 | 5.60 | 24.62 |
| 12 | 16.0 | 6.40 | 32.15 |
| 16 | 18.5 | 7.40 | 42.99 |

1 Template diameter ÷ 2.5 (average camera magnification)

Baseline Photographs

Stereoscopic color fundus photographs of fields 1 and 2, red-free photographs, and stereoscopic fluorescein angiograms of the study eye are obtained at the baseline to identify features of the choroidal neovascular (CNV) lesions which may affect the treatment benefit or visual outcome.

Fluorescein Angiogram

Evidence of CNV (Leakage on FA):

The entire fluorescein angiographic sequence is reviewed to determine if there is hyperfluorescent leakage consistent with the presence of CNV. The presence of other lesion components known as features that obscure the delineation of CNV are also noted, such as contiguous areas of blood, blocked fluorescence, or serous PED. The reader determines if CNV is indeed present and is the predominant lesion component (>50% of the lesion) or whether the area involved by the sum of all obscuring components predominates (CNV<50% of lesion). If no leakage from CNV is present, a "no" grade is indicated. Areas of staining fibrous tissue are considered as non-CNV components and are included in determining the percent of the lesion that is CNV.

Choroidal neovascular tissue can occur anywhere within the fundus. Field 2 is used to determine if the choroidal neovascular leakage underlies the geometric center of the foveal avascular zone (subfoveal) or whether it clearly spares the foveal center (not subfoveal). Depending on the presence of previous laser treatment and background retinal pigment epithelial abnormalities, it sometimes can be difficult to precisely delineate the foveal center; however, in some cases the reader can say with relative certainty that the CNV is very likely to be under the foveal center (probably subfoveal).

Lesion Components:

The entire neovascular lesion is studied throughout the fluorescein angiogram to determine the lesion components which are present. Each lesion component that may comprise a neovascular lesion is listed here, and the reader must identify whether each component is definitely present (yes), questionably present (questionable), or definitely absent (no). As performed in the MPS, the reader prepares a tracing of landmark vessels and lesion components using the dokumator and the available photographs.

Areas of classic CNV are identified if the angiogram shows an area of bright, well-demarcated hyperfluorescence in the early phase of the angiogram, with progressive dye leakage into the overlying subsensory retinal space in the late phase of the angiogram. A vascular or tubular matrix is variably present. When classic CNV is present the readers determine the relative area involved with this component and compare that area to the sum of the area involved with all other lesion components, if present. The reader determines if classic CNV is the predominant lesion component (>50%) or if the total of other components predominate (classic CNV<50%).

Occult CNV is identified when there is staining or leakage from a fibrovascular pigment epithelial detachment (PED) or when there is hyperfluorescent leakage at the level of the RPE that represents late leakage of an undetermined source. Fibrovascular PED represents areas of irregular elevation of the pigment epithelium consisting of speckled or granular hyperfluorescence that is not as bright as classic CNV, frequently appearing within one to two minutes after fluorescein injection (later than classic CNV), with persistence of staining or leakage of dye in the late frames. Late leakage of an undetermined source is areas of leakage at the level of the retinal pigment epithelium in the late phase of the angiogram without classic CNV or fibrovascular PED discernible in the early or middle phase of the angiogram to account for the leakage.

Areas of prior laser treatment are identified when the photographic materials show zones of hypopigmented or atrophic RPE, often with sharp margins with visualization of large caliber choroidal vessels within it, or sometimes even bare sclera. The fluorescein angiogram generally shows early central hypofluorescence followed by hyperfluorescent staining of the margins of the zone. Often, a feeder vessel to the recurrent area of CNV originates within an area of prior laser treatment; therefore, the presence of a feeder vessel may be helpful in recognizing an area of prior treatment. Even when the laser scar does not define the lesion border, the area of prior laser treatment is identified. When the center has indicated that the subject had prior laser treatment and there is no evidence on the photographs, the reader indicates no prior laser treatment component.

Any blood that is contiguous to other lesion components and is thick enough that it is interpreted as obscuring the readers' ability to detect underlying hyperfluorescence from CNV if it were present, is considered a lesion component itself. Very thin blood is not considered a lesion component nor is thick or thin blood that is noncontiguous to other lesion components.

Blocked fluorescence that is contiguous to other lesion components, visualized at any time during the transit, is considered a lesion component itself. This may correspond to pigment hyperplasia on color fundus photographs or possibly fibrous tissue, but will not correspond to visible blood. This is variably elevated but may be perceived as flat at the level of the RPE.

A serous pigment epithelial detachment that is contiguous to other lesion components is also considered a lesion component itself. Serous PED is identified when there is a regular degree of elevation to the pigment epithelium, often dome shaped in its contour, with sharply demarcated borders. These regions hyperfluoresce early, generally of a uniform nature, and have persistent hyperfluorescence and constant borders in the late phases of the angiogram. They lack a granular appearance and the perimeter of the configuration is often regularly shaped and round.

Area of Lesion—MPS Disc Areas:

The lesion to be measured is comprised of CNV (classic plus occult CNV, if present), contiguous natural scaning associated with the CNV (such as non-geographic atrophy or fibrosis which may stain rather than leak during angiography), and features that obscure the boundaries of CNV such as contiguous blood, blocked fluorescence (either due to fibrosis or pigmentation) and/or serous PEDs. Previous laser treatment, if present is considered in addressing question 9, but it is not a lesion component to be used in size calculations. Contiguous zones of geographic atrophy are not included in the area.

The Zeiss 30° MPS disc area template is used for all photographs taken on cameras with magnifications ranging from 2.4× to 2.6×. This template is placed directly over a representative frame of the fluorescein angiogram that includes all lesion components, prior to significant leakage. The template is centered with reference to the center of the lesion and the circle is selected that best incorporates all aspects of the lesion. If the lesion is irregularly shaped such that a portion or portions goes beyond the perimeter of the circle, then the reader excises this portion of the lesion from the exterior of the circle and incorporates it into available portions of the circle. If no areas of the circle are "unavailable" (meaning unoccupied by lesion) for portions of the lesion that go beyond the circle margins then the next size circle is the more appropriate choice. This question estimates the gross area of the central macula that is involved by the choroidal neovascular process. Categorical assignments are as follows: <1, <2, <3, <4, <5, <6, <9, <12, <16, and >16 disc areas.

EXAMPLE 3

Treatment of Occult Choroidal Neovascular Lesions with Verteporfin PDT

Subjects having, suspected of having, or otherwise afflicted with occult neovascular lesions were evaluated for best corrected visual acuity as outlined in Example 1, and their lesion size determined angiographically as outlined in Example 2. Subjects were included if they had a best corrected vision of at least 50 letters, corresponding to approximately 20/100, and had a CNV lesion that is occult, with no evidence of classic CNV. The greatest linear dimension of the entire CNV lesion was 5.4 square millimeters, corresponding to 9 Disc Areas. Subjects were evaluated for visual acuity and lesion size about 1 week prior to treatment. Subjects were randomly assigned to a treatment group and a placebo group.

For each subject in the treatment group, a 15 mg-vial of liposomally-formulated verteporfin (Verteporfin for Injection (Visudyne™) was reconstituted with 7 mL of sterile water for injection to provide 7.5 mL containing a final concentration of 2 mg/mL. The volume of reconstituted drug required to achieve a dose of 6 mg/M$^2$ (based upon the height and weight of the subject, calculated from a nomogram) was withdrawn from the vial and diluted with 5% dextrose for injection to make a total infusion volume of 30 mL. The full infusion volume was administered intravenously over 10 minutes using an appropriate syringe pump and in-line filter. Fifteen minutes after the start of the infusion, light was administered to the lesion from a diode laser through a fiber optic delivered via a slit lamp, and utilizing a suitable lens. A light dose of 50J/cm$^2$ was applied at a fluency rate of 600 mW/cm$^2$, 50J/cm$^2$ (83 second exposure). Each subject in the placebo group received an identical treatment, except that the infusion consisted entirely of 30 mL 5% dextrose for infusion, and did not contain any Verteporfin for Injection.

Subjects were evaluated by fluorescein angiography approximately every three months, and their best corrected visual acuity was assessed. Subjects were retreated if evidence of CNV leakage was detected by fluorescein angiography.

The visual acuity of the subjects at 24 months after the initial treatment is shown in Table 2.

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

The invention claimed is:

1. A method for treating an occult choroidal neovascular (CNV) lesion in a subject comprising
    selecting a subject with an occult CNV lesion comprising an occult component of >50% and <100% of the lesion and assessed as having either (a) a small lesion with a size less than 5 disc areas, or (b) poor visual acuity of less than 65 letters prior to treatment, or both (a) and (b); and
    providing photodynamic therapy (PDT) to the subject having said CNV lesion, wherein said PDT comprises the administration of a photosensitizer (PS), wherein said PS is a green porphyrin.

2. The method of claim 1 wherein said subject was assessed by determining the size of said lesion and/or determining the best corrected visual acuity of the subject.

3. The method of claim 1 wherein the small lesion has a size less than 4 disc areas.

4. The method of claim 1, wherein said occult CNV lesion is in a subject afflicted or diagnosed with age-related macular degeneration (AMD).

TABLE 2

Impact of Baseline Visual Acuity (VA) Score and Lesion Size on Outcome of Treatment with Verteporfin PDT of Occult CNV

| Visual Acuity | Lesion Size | 15 Letter Response Rate[1] Difference V[3]-P[4] | p-value | 30 Letter Response Rate[2] Difference V-P | p-value | Mean VA Difference | Sample Size n(V) | n(P) |
|---|---|---|---|---|---|---|---|---|
| <65 Letters | All | 33.8% | 0.0004 | 27.5% | 0.0007 | 11.7 | 79 | 41 |
| <65 Letters | ≦4DA | 43.8 | .003 | 19.4 | 0.03 | 12.3 | 36 | 16 |
| <65 Letters | ≧4DA | 21.5 | 0.07 | 30.0 | 0.01 | 9.4 | 41 | 25 |
| ≧65 Letters | All | −3.9 | 0.18 | 8.5 | 0.34 | 1.5 | 87 | 51 |
| ≧65 Letters | ≦4DA | 12.5% | .30 | 26.8% | 0.36 | 9.3 | 44 | 23 |
| ≧65 Letters | ≧4DA | −24% | 0.046 | −5.3% | 0.65 | −3.3 | 43 | 27 |

[1]Percent of subjects losing less than 15 letters
[2]Percent of subjects losing less than 30 letters
[3]Subjects treated with verteporfin PDT
[4]Subjects treated with placebo 5. The method of claim 1, wherein the PS is administered at a concentration ranging between about 2 to 8 mg/m$^2$ (PS/body surface area of subject).

6. The method of claim 5, wherein the PS is administered at a concentration of 6 mg/m$^2$.

7. The method of claim 1, wherein the green porphyrin is selected from BPD-DA, BPD-DB, BPD-MA, BPD-MB, EA6, and B3.

8. The method of claim 7, wherein the green porphyrin is BPD-MA.

9. The method of claim 1, wherein the PS is coupled to a specific binding ligand.

10. The method of claim 1, wherein the PS is formulated with a carrier.

11. The method of claim 10, wherein the formulation is selected from the group consisting of a liposome, emulsion, or aqueous solution.

12. The method of claim 1, wherein said PDT comprises irradiation with electromagnetic radiation containing wavelengths in the visible light spectra.

13. The method of claim 12, wherein the irradiation provides between 12.5 J/cm$^2$ and 100 J/cm$^2$.

14. The method of claim 13, wherein said irradiation occurs between 5 to 30 minutes after administration of a photosensitizer.

15. The method of claim 1, wherein the PS is administered at a concentration ranging between about 10 μg/kg to 100 mg/kg (PS/body weight of subject).

16. The method of claim 1, wherein a resulting loss of visual acuity is less with treatment than without treatment.

17. The method of claim 7, wherein the green porphyrin is EA6.

* * * * *